United States Patent [19]
Squicciarini

[11] Patent Number: 5,947,725
[45] Date of Patent: Sep. 7, 1999

[54] CASTING ELEMENTS TO BE APPLIED DIRECTLY ON THE ARTICULATOR FOR CASTING GYPSUM MODELS FOR DENTAL PROSTHESIS

[76] Inventor: Gaetano Squicciarini, No. 350, Via Conca dOro, 00141 Rome, Italy

[21] Appl. No.: 08/902,357

[22] Filed: Jul. 29, 1997

[30] Foreign Application Priority Data

Jul. 29, 1996 [IT] Italy .............................. RM960173 U

[51] Int. Cl.$^6$ .................................................. A61C 11/00
[52] U.S. Cl. .................................................. 433/60
[58] Field of Search ................................ 433/60

[56] References Cited

U.S. PATENT DOCUMENTS

| | | | |
|---|---|---|---|
| 537,812 | 4/1895 | Bragg | 433/60 |
| 2,337,036 | 12/1943 | Erdle | 433/34 |
| 3,161,917 | 12/1964 | Wiland | 249/54 |
| 3,221,408 | 12/1965 | Scullin | 433/60 |
| 3,650,032 | 3/1972 | Kestler | 433/53 |
| 3,844,040 | 10/1974 | Willis | 433/60 |
| 4,203,219 | 5/1980 | Wiener | 433/74 |
| 4,283,173 | 8/1981 | Browne et al. | 433/34 |
| 4,300,884 | 11/1981 | Camacho | 433/74 |
| 4,337,039 | 6/1982 | Martin et al. | 433/60 |
| 4,494,934 | 1/1985 | Huffman | 433/213 |
| 4,522,591 | 6/1985 | Braun et al. | 433/60 |
| 4,842,242 | 6/1989 | Huffman | 433/60 |
| 5,647,744 | 7/1997 | Squicciarini | 433/34 |
| 5,658,143 | 8/1997 | Kuperman | 433/60 |

FOREIGN PATENT DOCUMENTS

| | | |
|---|---|---|
| 0277027 A2 | 8/1988 | European Pat. Off. . |
| 4028728 A1 | 3/1992 | Germany . |
| 42 22 699 A1 | 1/1994 | Germany . |
| 44 09 931 A1 | 9/1995 | Germany . |

OTHER PUBLICATIONS

Cover sheet and a single definition page of "Concise Chemical and Technical Dictionary", Third Enlarged Edition, Chemical Publishing Co., Inc. (1974), 200 Park Avenue South, New York, NY 10003.

Cover sheet, copyright page, and a single definition page of "Webster's New World Dictionary of the American Language", Second College Edition, Prentice Hall Press/Simon & Schuster (1984).

Color Brochure entitled, "The Future of Plaster Working in the Dental Technician's Art", by Gaetano Squicciarini, Via Conca d'Oro, 352–00141 Rome, Italy. (no date available).

Primary Examiner—John J. Wilson
Attorney, Agent, or Firm—Smith, Gambrell & Russell, LLP; Beveridge, DeGrandi, Weilacher & Young Intellectual Property Group

[57] ABSTRACT

A casting element formed of a pliable material and shaped so as to be applied directly to an articulator support component. A casting element set is provided, particularly when the articulator has different configured upper and lower support components to which the casting elements are releasably set in position. The casting elements preferably include a pliable main body such as one of rubber or other conforming material such as silicone and are shaped to conform with the particular articulators' support configuration. This arrangement allows for casting of models for dental prosthesis directly on the articulator.

5 Claims, 5 Drawing Sheets

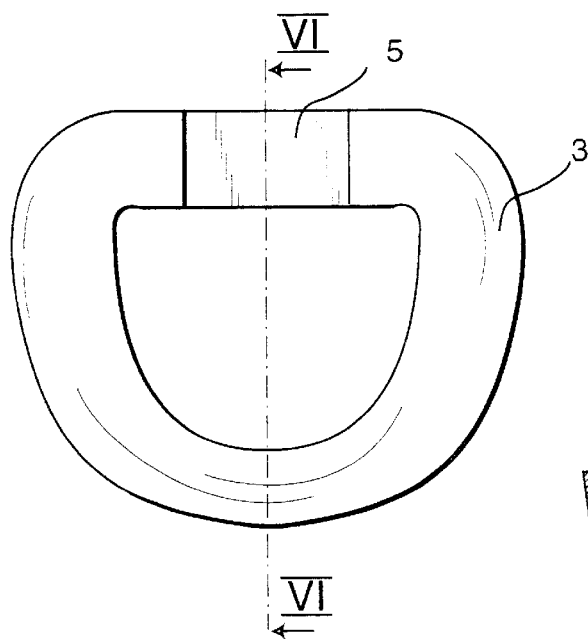
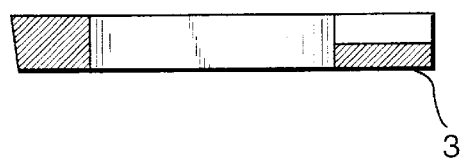
FIG. 5　　　　FIG. 6
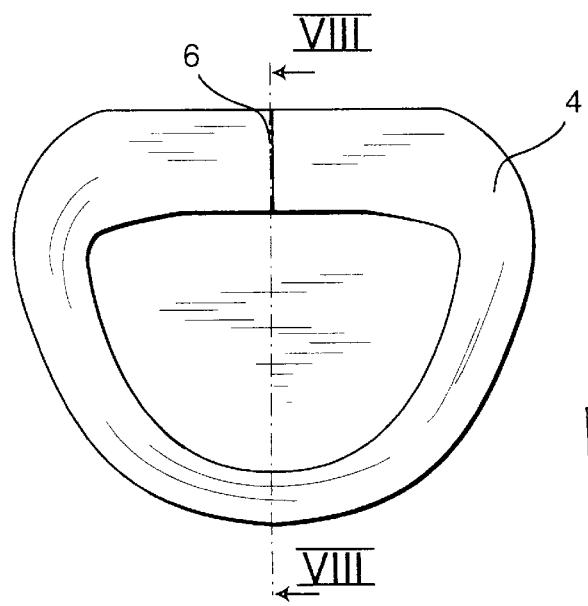
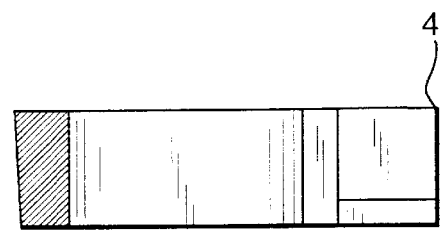
FIG. 7　　　　FIG. 8

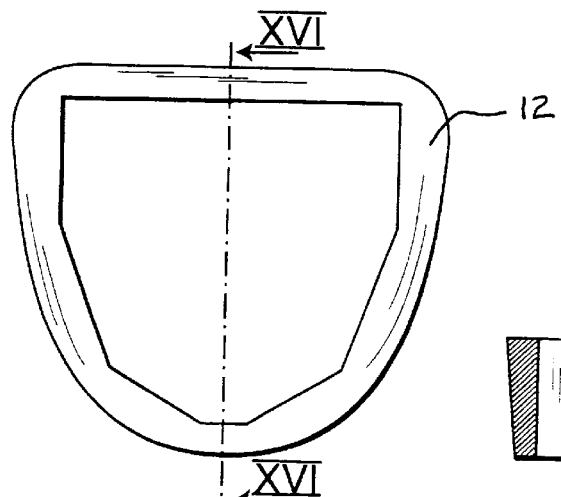
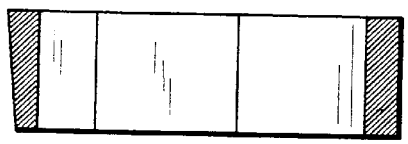
FIG. 15  FIG. 16
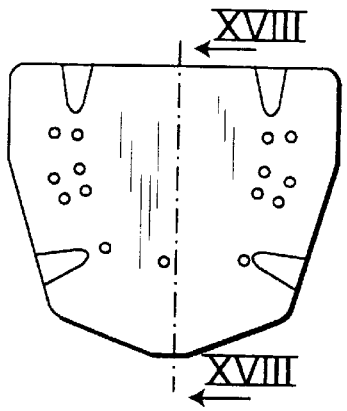
FIG. 17  FIG. 18
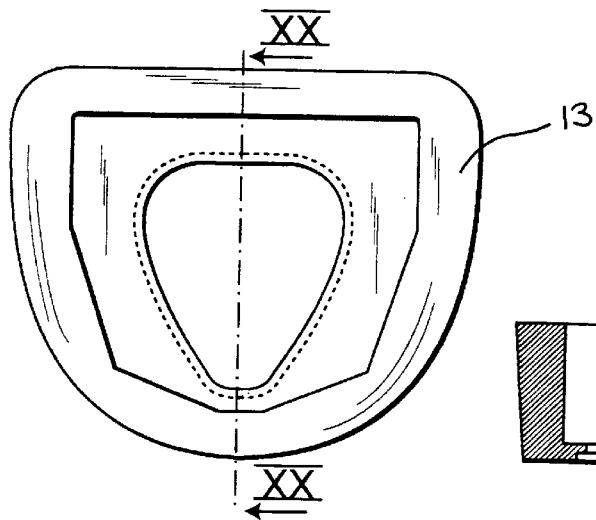
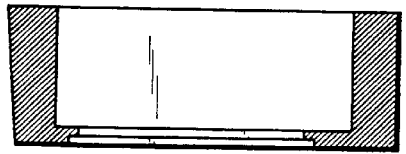
FIG. 19  FIG. 20

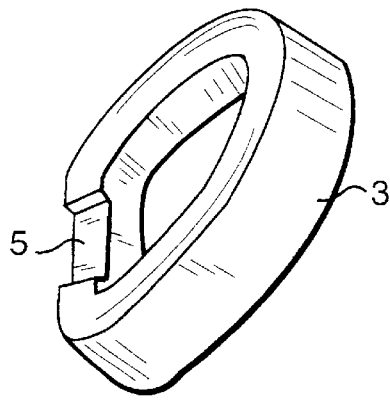
FIG. 21a
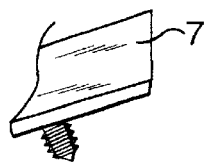
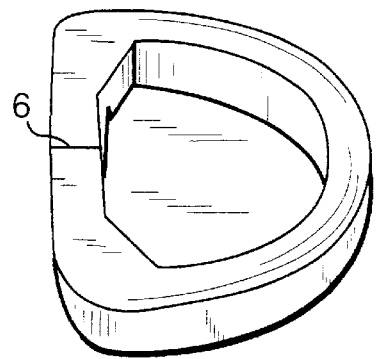
FIG. 21b
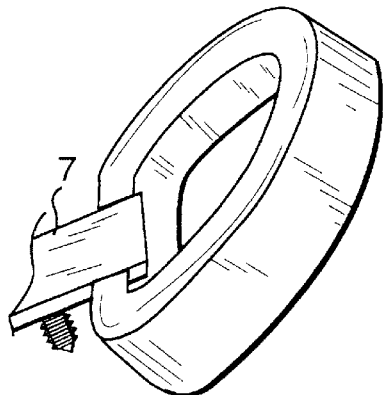
FIG. 22a
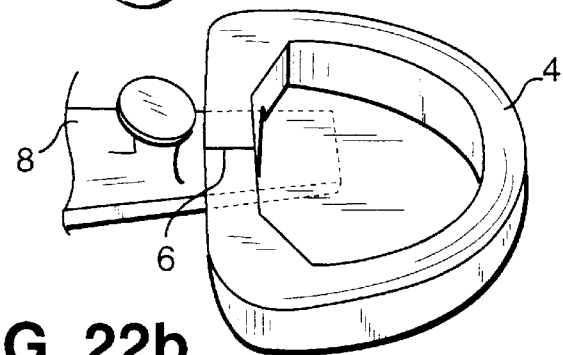
FIG. 22b

CASTING ELEMENTS TO BE APPLIED DIRECTLY ON THE ARTICULATOR FOR CASTING GYPSUM MODELS FOR DENTAL PROSTHESIS

FIELD OF THE INVENTION

The present invention relates to casting elements to be applied directly on the articulator, for casting gypsum models for dental prosthesis.

BACKGROUND OF THE INVENTION

By the patent application N° RM94A000500 filed on Jul. 27, 1994, the Applicant has filed an application concerning a set of casting elements for casting gypsum models for dental prosthesis.

Before the filing of the above mentioned patent application, the casting of gypsum for the realisation of models for dental prosthesis was realised manually, i.e. casting the gypsum directly without any constraint.

This solution gave a very coarse product, which to be positively realised must be subjected to various finishing operations.

Further, this kind of solution does not provide for a model height that is set according to a specific needing.

As to a kind of work usually named Zeiser, requiring the introduction of pins on a Plexiglas plate, remarkably complicated apparatuses are employed, said apparatuses being difficult to be used and not allowing to obtain an optimum result.

In view of the above, the Applicant has realised in the previous patent application, a set of elements for making a casting for the realisation of gypsum models and for the subsequent realisation of prosthesis which allows one to easily, precisely and rapidly obtain gypsum models.

The solution suggested by the Applicant provided the realisation of rubber material elements, having different sizes, in order to be able to realise every kind of model, so shaped to obtain both palatal and lingual models.

In this way, a modern system was obtained, said system being very simple and fast during the casting of gypsum impressions, thus offering a great saving of time, of workers and of money.

Furthermore, the solution suggested provided a finishing, so that as soon as the impression was released, by the use of a known articulator, work could be immediately started without the use of a gypsum articulator. Its square and smooth shape provided for a precise and direct introduction on the articulator.

SUMMARY OF THE INVENTION

Now, the applicant has realised a series of further elements to complete what was already suggested in the previous patent application.

Particularly, casting elements are suggested for the realisation of gypsum models for dental prosthesis to be applied directly on the articulators.

The present invention casting elements for is thus directed at casting gypsum models for dental prosthesis, characterised in that they are shaped in such a way to be couplable with the upper part and with the lower part of the articulator.

Preferably, according to the invention, said elements are made up of rubber material, preferably of silicone material.

According to the invention, the casting elements can house a Plexiglas® or metallic material plate provided with a central magnet for the realisation of removable models.

Still according to the invention, the casting elements are realised to obtain fixed models.

Furthermore, according to the invention, said elements can be coupled with metal, plastic basis or with basis made up of another material.

BRIEF DESCRIPTION OF THE DRAWINGS

The present invention will be now described, for illustrative but not limitative purposes, according to its preferred embodiments, with particular reference to the figures of the enclosed drawings, wherein:

FIG. 5 is a top view of a first element according to the invention for a second kind of articulator;

FIG. 6 is a section view along line VI—VI of FIG. 5;

FIG. 7 is a top view of a second element according to the invention for a second kind of articulator;

FIG. 8 is a section view along line VII—VII of FIG. 7;

FIG. 15 is a top view of a first element according to the invention for a fourth kind of articulator;

FIG. 16 is a section view along line XVI—XVI of FIG. 15;

FIG. 17 is a top view of a plate to be mounted of the element of FIG. 15;

FIG. 18 is a section view along line XVII—XVII of FIG. 17;

FIG. 19 is a top view of a second element according to the invention for a fourth kind of articulator;

FIG. 20 is a section view along line XX—XX of FIG. 19; and

FIGS. 21a, 21b and 22a, 22b show in sequence the assembly of the elements of FIGS. 5–8 on the relevant articulator.

In the various figures some examples of elements according to the present invention for different kinds of articulators are shown for illustrative purposes it not being possible to illustrate every kind of articulator.

In any case, it will be evident to those skilled in the art that according to the teachings of the present invention, it will be possible to realise rubber material elements suitable to the upper and lower part of any kind of articulator, even different with respect to those shown in the enclosed drawings.

Figure 1:
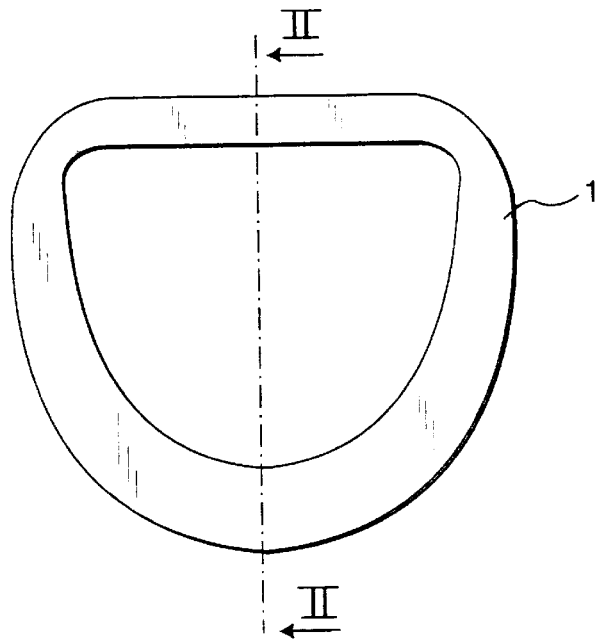
FIG. 1 is a top view of a first element according to the invention for a first kind of articulator.
Figure 2:
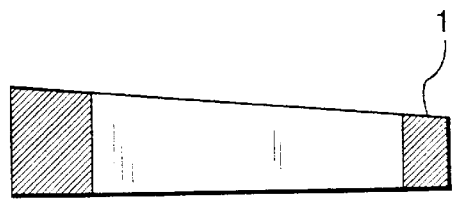
FIG. 2 is a section view along line II—II of FIG. 1.
Figure 3:
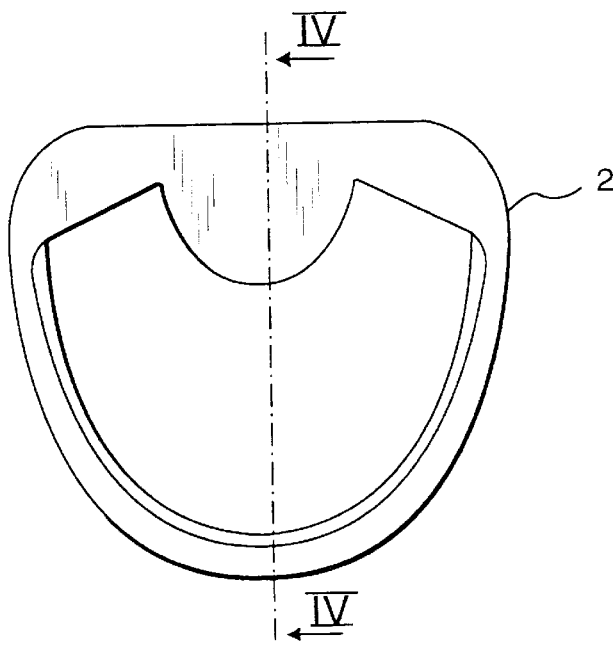
FIG. 3 is a top view of a second element according to the invention for a first kind of articulator.
Figure 4:
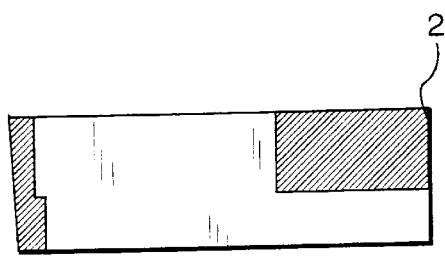
FIG. 4 is a section view along line IV—IV of FIG. 3.

In FIGS. 1–4 a first element 1 and a second element 2 are shown, which are to be coupled with a first articulator, not shown, particularly with the upper part and with lower part.

In this case, the coupling is simply realised conforming the shape of the rubber material element, preferably silicone material, to the shape of the articulator plates.

Elements 3 and 4 shown in FIGS. 5–8 instead have respectively, a rear seat 5 and a slot 6 for the coupling with the articulator.

In FIGS. 21a, 21b, 22a, 22b it is shown how the elements 4 and 5 couple with the upper part 7 and the lower part 8 of the subject articulator.

Figure 9:
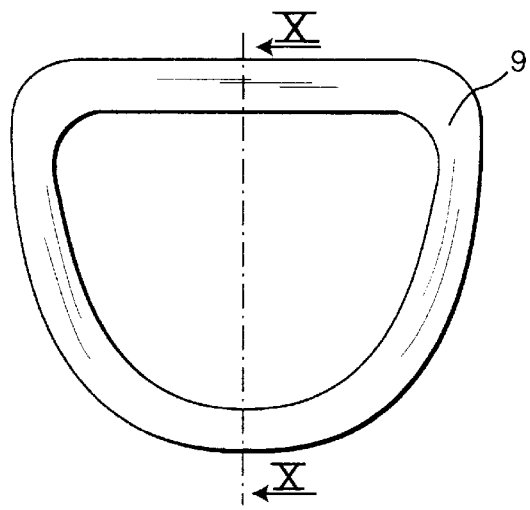
FIG. 9 is a top view of a first element according to the invention for a third kind of articulator.
Figure 10:
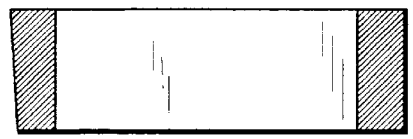
FIG. 10 is a section view along line X—X of FIG. 9.
Figure 11:
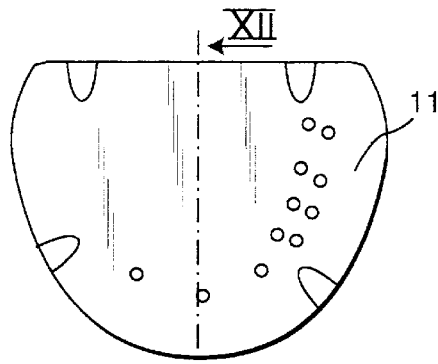
FIG. 11 is a top view of a plate to be mounted of the element of FIG. 9.
Figure 12:
FIG. 12 is a section view along line XII—XII of FIG. 11.
Figure 13:
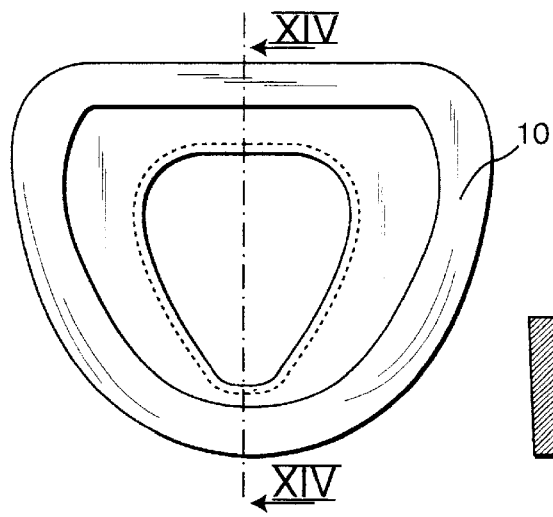
FIG. 13 is a top view of a second element according to the invention for a third kind of articulator.
Figure 14:
FIG. 14 is a section view along line XIV—XIV of FIG. 13.

In FIGS. 9–14 two elements 9 and 10 according to the invention are shown, to be used in combination with a Plexiglas® plate 11.

In this case, the coupling between the elements 9 and 10 and the articulator, not shown, occurs by suitably shaping said elements 9 and 10 in such a way to conform to the shape of the upper and lower parts of the articulator.

In FIGS. 15–20 there is instead shown two elements 12 and 13 according to the invention to be used in combination with a Plexiglas plate 14.

Also in this case, the coupling between elements 12 and 13 and the articulator, not shown, occurs suitably shaping said element 12 and 13 in such a way to correspond to the shape of the upper and lower parts of the articulator.

The present invention has been described for illustrative but not limitative purposes, according to its preferred embodiments, but it is to be understood that modifications and/or changes can be introduced by those skilled in the art without departing from the relevant scope as defined in the enclosed claims.

I claim:

1. A casting element for casting a model for dental prosthesis, characterised in that said casting element is pliable and shaped in such a way as to be couplable with at least one of an upper part and a lower part of an articulator wherein said casting element has a hole formed therein defined by at least one interior side wall of said casting element which side wall is configured to sufficiently correspond with and extend about a component of the articulator to provide for a coupling between said pliant casting element and the component of the articulator, wherein said hole is a throughhole opening out both at an upper and lower surface of said casting element, and wherein said throughhole is a stepped throughhole formed by a corresponding stepped side wall of said casting element.

2. A casting element set for casting models for dental prosthesis, comprising a first casting element and a second casting element, said first casting element being pliable and shaped in such a way as to be couplable with at least one of an upper part and a lower part of the articulator, and said second casting element being shaped so as to be couplable to an opposite one of the upper and lower parts of the articulator, wherein each of said first and second casting elements is formed of a pliable material and each has an interior throughhole defined by an interior side wall of said casting element, and wherein said second casting element has a stepped throughhole formed therein defined by different peripheral dimensions in the internal side wall of said second casting element.

3. A casting element set as recited in claim 2, wherein said first casting element has a different interior side wall configuration than that of said second casting element.

4. A casting element as recited in claim 2, wherein said second casting element has a seat opening out at one end at the interior side wall of said second casting element and an opposite end opening out at an exterior surface of said second casting element.

5. A casting element as recited in claim 2, wherein said second casting element has a slot extending from the interior side wall of said second casting element to an external surface of said second casting element.

* * * * *